(12) United States Patent
Stark et al.

(10) Patent No.: US 8,962,070 B2
(45) Date of Patent: Feb. 24, 2015

(54) METHOD FOR THE DEPOSITION OF A METAL LAYER COMPRISING A BETA-AMINO ACID

(75) Inventors: Franz-Josef Stark, Zülpich (DE); Christoph Werner, Düsseldorf (DE)

(73) Assignee: Enthone Inc., West Haven, CT (US)

( * ) Notice: Subject to any disclaimer, the term of this patent is extended or adjusted under 35 U.S.C. 154(b) by 38 days.

(21) Appl. No.: 13/382,131

(22) PCT Filed: Jul. 6, 2010

(86) PCT No.: PCT/US2010/041077
§ 371 (c)(1),
(2), (4) Date: Mar. 7, 2012

(87) PCT Pub. No.: WO2011/003116
PCT Pub. Date: Jan. 6, 2011

(65) Prior Publication Data
US 2012/0156387 A1  Jun. 21, 2012

(30) Foreign Application Priority Data

Jul. 3, 2009 (EP) ..................................... 09008744
Apr. 22, 2010 (EP) ..................................... 10004296

(51) Int. Cl.
*B05D 5/12* (2006.01)
*C23C 18/16* (2006.01)
*C07C 229/08* (2006.01)
*C07C 229/12* (2006.01)
*C07C 229/16* (2006.01)
*C07C 229/22* (2006.01)
*C07C 237/06* (2006.01)
*C07C 309/14* (2006.01)
*C23C 18/31* (2006.01)
*C23C 18/32* (2006.01)
*C23C 18/34* (2006.01)
*C23C 18/36* (2006.01)
*C23C 18/38* (2006.01)
*C23C 18/40* (2006.01)
*C23C 18/42* (2006.01)
*C23C 18/44* (2006.01)
*C23C 18/48* (2006.01)
*C23C 18/50* (2006.01)

(52) U.S. Cl.
CPC ........... *C23C 18/1601* (2013.01); *C07C 229/08* (2013.01); *C07C 229/12* (2013.01); *C07C 229/16* (2013.01); *C07C 229/22* (2013.01); *C07C 237/06* (2013.01); *C07C 309/14* (2013.01); *C23C 18/31* (2013.01); *C23C 18/32* (2013.01); *C23C 18/34* (2013.01); *C23C 18/36* (2013.01); *C23C 18/38* (2013.01); *C23C 18/40* (2013.01); *C23C 18/42* (2013.01); *C23C 18/44* (2013.01); *C23C 18/48* (2013.01); *C23C 18/50* (2013.01)

USPC .......... 427/97.9; 427/99.5; 427/304; 427/437

(58) Field of Classification Search
USPC ................................ 427/97.9, 99.5, 304, 437
See application file for complete search history.

(56) References Cited

U.S. PATENT DOCUMENTS

| | | | | |
|---|---|---|---|---|
| 2,935,425 | A * | 5/1960 | Gutzeit et al. ................. | 427/438 |
| 3,515,564 | A * | 6/1970 | Baudrand et al. ............. | 106/1.22 |
| 3,846,138 | A * | 11/1974 | Gulla ........................... | 106/1.26 |
| 4,171,225 | A * | 10/1979 | Molenaar et al. ............. | 106/1.23 |
| 4,503,131 | A * | 3/1985 | Baudrand ...................... | 428/672 |
| 5,149,566 | A * | 9/1992 | Morton et al. ................ | 427/235 |
| 5,258,061 | A * | 11/1993 | Martyak et al. ............... | 106/1.22 |
| 6,800,121 | B2 * | 10/2004 | Shahin .......................... | 106/1.22 |
| 2004/0086646 | A1 * | 5/2004 | Brandes et al. ................ | 427/304 |
| 2004/0144285 | A1 * | 7/2004 | Stark et al. .................... | 106/1.27 |
| 2008/0073218 | A1 * | 3/2008 | Ishikawa et al. ................ | 205/50 |

FOREIGN PATENT DOCUMENTS

| | | |
|---|---|---|
| GB | 785695 | 11/1957 |
| GB | 785696 | 11/1957 |
| GB | 2231063 | 11/1990 |
| JP | 2003-113478 | * 4/2003 |
| JP | 2005126734 | 5/2005 |
| JP | 2007162069 | 6/2007 |
| WO | 9105085 | 4/1991 |

OTHER PUBLICATIONS

Abstract of JP2007162069; Jun. 28, 2007.
European Search Report, EP Application No. 09008744.6, dated Nov. 18, 2009, 8 pages.
European Search Report, EP Application No. 10004296.9, dated Sep. 20, 2010, 7 pages.
Ke Wang et al., "Investigation into the Roles of Sulfur-Containing Amino Acids in Electroless Nickel Plating Bath", Industrial & Engineering Chemistry Research, 2008, 47 (17), pp. 6517-6524.
International Search Report and Written Opinion, PCT/US2010/041077, dated Apr. 23, 2014, 19 pages.
International Preliminary Report on Patentability, PCT/US2010/041077, dated Apr. 29, 2014, 12 pages.

* cited by examiner

*Primary Examiner* — Brian K Talbot
(74) *Attorney, Agent, or Firm* — Senniger Powers LLP

(57) ABSTRACT

The present invention relates to an electrolyte for the electroless deposition of a metal layer on a substrate, wherein the electrolyte is free of heavy metal stabilizers, cyanides, selenium compounds and sulfur compounds comprising sulfur in an oxidation state between −2 and +5, and in which instead a β-amino acid is used as stabilizer. In particular, the inventive electrolyte can comprise 3-aminopropionic acid, 3-aminobutyric acid, 3-amino-4-methylvaleric acid, and 2-aminoethane-sulfonic acid. Furthermore, the invention is directed to a method for the electroless deposition of metal layers utilizing an inventive electrolyte as well as the use of β-amino acids as stabilizer in electrolytes for the electroless deposition of metal layers in general.

24 Claims, No Drawings

METHOD FOR THE DEPOSITION OF A METAL LAYER COMPRISING A BETA-AMINO ACID

REFERENCE TO RELATED APPLICATIONS

This application is the U.S. national stage application of International Patent Application No. PCT/US2010/041077, filed Jul. 6, 2010, and claims the benefit of European Application No. 09008744.6, filed Jul.3, 2009 and European Application No. 10004296.9, filed Apr. 22, 2010, the entire disclosures of which are incorporated herein by reference.

BACKGROUND OF THE INVENTION

The present invention relates to an electrolyte as well as a method for the electroless deposition of metals, particularly layers of nickel, copper, cobalt, boron or gold, as well as layers of alloys comprising at least one of the aforementioned metals as alloying metal. Furthermore, the present invention relates to the use of β-amino acids as stabilizers in electrolytes for the electroless deposition.

The present invention further relates to an organic stabilizer for electroless plating processes, and an electrolyte for the electroless deposition of a metal layer on a substrate, comprising a metal ion source for the metal to be deposited, a reducing agent, a complexing agent, a stabilizer and preferably an accelerator, as well as a method for the electroless deposition of a metal layer on a surface from an electrolyte according to the invention. Further the invention relates to a use of at least one carboxylic acid and/or at least one salt of a carboxylic acid.

Among electrolytic methods for the plating of substrates with metal layers, electroless plating methods have long been known from the state of the art. By electroless plating, also known as chemical plating, the coating of almost every metal and a huge number of non-conductive substrate surfaces is possible. The electroless deposited metal layers differ from the galvanically deposited metal layers, i. e. those layers deposited by the use of an external current, in physical as well as mechanical aspects. Often, metal alloy layers with non-metal elements, like for example cobalt/phosphor, nickel/phosphor or boron carbide layers are deposited by means of electroless deposition methods. In this respect, electroless deposited layers in many cases differ also in their chemical nature from the galvanically deposited layers.

One major advantage of the electroless deposited metal layer is the outline accuracy of the layer thickness of the deposited layer independent from the substrate geometry, which feature makes the electroless methods the first choice in the area of printed circuit boards (PCB) manufacturing, and here especially for the metallization of through hole contacts, vias and trenches.

Many times, electroless methods are also used for the coating of other non-conductive substrates, like for example plastic substrates, to render the surface of such substrates conductive and/or to change the appearance of the substrate in aesthetic respect. Furthermore, by the deposited layers, the material properties of the coated substrate can be improved or amended. Especially, the corrosion resistance or the hardness of the surface and/or the wear resistance of the substrate can be improved.

Electroless plating methods are based on an autocatalytic process, in which process the metal ions comprised in the electrolytes are reduced to the elemental metal by a reducing agent which is oxidized during this redox reaction.

A reducing agent commonly used in the field of electroless deposition of metals on substrate surfaces is sodium hypophosphite. However, also other reducing agents are used in dependency of the metals to be deposited.

U.S. Pat. No. 6,146,702 discloses an electroless nickel cobalt phosphorus composition and plating process. The process is provided for enhancing the wear resistance of aluminium and other materials by depositing on the substrate a nickel, cobalt, phosphorus alloy coating using an electroless plating bath to provide a plated alloy having a cobalt content of at least about 20% by weight and a % Co/% P weight ratio of at least about 5.

European patent application EP 1 413 646 A2 discloses, for example, an electrolyte for the electroless deposition of nickel layers having internal compressive stress. The electrolyte disclosed in this application comprises a metal salt of the metal to be deposited, a reducing agent, a complexing agent, an accelerator, and a stabilizer.

Here, the accelerator is used to increase the deposition rate of the metal on the substrate surface.

In known electroplating baths it is necessary to use a stabilizer to avoid the uncontrolled plateout (wild deposition) of the electrolyte, which means the unregulated wild deposition of metal on the substrate surface. Hitherto, in the state of the art, heavy metals like lead, bismuth, zinc or tin are used as stabilizers. According to common environmental regulations [ROHS (Restriction of the use of certain hazardous substances), WEEE (Waste electrical and electronic equipment), ELV (End of lifetime of vehicles)] prior to the disposal of expended electrolytes and the co-deposition of heavy metals such heavy metals have to be withdrawn from the aqueous solution used as electrolyte in an adequate treatment step. Also when the heavy metals are comprised in the electrolyte only in small amounts, such a treatment causes additional expenses for the disposal. Therefore, the use of heavy metal in electrolytes for the deposition of metal layers has to be avoided. In some other types of electrolytes, like for example electrolytes for the electroless deposition of copper, cyanides are used as stabilizers. Like heavy metal ions, such cyanides are subject to environmental regulations. The same is true for selenium compounds which are also commonly used as stabilizers.

Furthermore, there is an interest in the art of metal plating to avoid sulfur compounds which comprise sulfur in an oxidation state between −2 and +5, since these compounds are also subject to environmental regulations. However, by now such compounds are often needed in the electrolytes to gain good plating results.

SUMMARY OF THE INVENTION

It is therefore an object of the present invention to provide a formulation for electroless plating that is stabilized against uncontrolled plateout of the metal to be deposited.

It is a more particular object of various preferred embodiments of the pending application to provide an electrolyte for the electroless deposition which is free of heavy metal stabilizers, cyanides, selenium compounds, and/or sulfur compounds comprising sulfur in an oxidation state between −2 and +5.

This object is solved by an aqueous electrolyte for the electroless deposition of a metal layer on a substrate, comprising a metal ion source for the metal to be deposited, a reducing agent, a complexing agent, an accelerator, and a stabilizer, characterized in that the electrolyte comprises as stabilizer a β-amino acid.

It is a further object of the present invention to provide an improved stabilizer for electroless plating processes, and a new electrolyte as well as a method for the electroless deposition of a metal layer having improved properties.

The invention is particularly directed to a formulation useful in electroless deposition of a metal layer on a substrate wherein the formulation comprises a source of a cation of the metal to be deposited, a reducing agent, a complexing agent, and a stabilizer selected from the group consisting of β-amino acids, β-amino acid derivatives and combinations thereof. The ratio of the total equivalent β-amino acid concentration to the molar concentration of said reducing agent is no greater than about 0.07 equivalents/mole.

The invention is further directed to a formulation useful in electroless deposition of a metal layer on a substrate, said formulation comprising a source of a cation of the metal to be deposited, a reducing agent, a complexing agent, and a stabilizer selected from the group consisting of β-amino acids, β-amino acid derivatives and combinations thereof, and at least one additional carboxyl compound selected from the group consisting of carboxylic acids and salts thereof. The ratio of the total equivalent β-amino acid concentration to the difference between the total equivalent carboxyl concentration of the formulation and the total equivalent β-amino acid concentration is not greater than about 0.028.

In a further aspect, the invention is directed to an aqueous electroless plating bath comprising between about 0.05 and about 0.2 moles/liter of the cation of a metal to be electrolessly deposited on a substrate, between about 0.05 and about 1.25 moles/liter of a reducing agent, between about 0.1 and about 2 moles/liter of a complexing agent, between about 0.002 and about 0.25 moles/liter of an accelerator, and between about 0.0005 and about 0.015 moles/liter total equivalent β-amino acid.

In a still further aspect, the invention is directed to an aqueous electroless plating bath comprising a metal to be electrolessly deposited on a substrate, a reducing agent, a complexing agent, and an amide of a β-amino acid.

The invention is also directed to a process for the preparation of an electroless plating solution. In accordance with the process, a β-amino acid or a β-amino acid derivative is contacted with a carboxyl component in an aqueous medium to form a premixture. The premixture is combined with an aqueous solution comprising a source of a cation of the metal to be deposited.

In another aspect, the invention is directed to a process for preparation of an electroless plating solution comprising. In accordance with the process, a first solution comprising a first metal cation is passed across a first face of a dialysis membrane comprising a cation exchange resin. The first metal cation comprising a metal to be deposited from the electroless plating bath. A second solution comprising a β-amino acid or a β-amino acid derivative and another cation is passed across the face of said membrane opposite the first face. A first metal cation of the first solution is exchanged with said another metal cation of the second solution, thereby converting said second solution to a formulation useful in electroless plating.

The invention is also directed to a method for the electroless deposition of a metal layer on a substrate comprising contacting the substrate to be plated with a plating formulation of the invention and/or as prepared in accordance with the methods of the invention.

DESCRIPTION OF THE PREFERRED EMBODIMENT

Surprisingly, it was found that β-amino acids are capable to replace heavy metal stabilizers, cyanides, selenium compounds as well as sulfur compounds comprising sulfur in an oxidation state between −2 and +5 in electrolytes for the electroless deposition of metal layers, totally.

While not being bound to this theory, the applicant believes that the β-amino acids due to their indirectly adjacent amino group and carboxyl group are capable to at least temporarily jam the active centers on the substrate surface which are responsible for the uncontrolled deposition. So the wild deposition of the metals can be avoided. Additionally, also the foreign ions comprised in the electrolyte which are responsible for the wild deposition, too, are inactivated by the used β-amino acid.

A further benefit of the inventive electrolyte and the inventive use of β-amino acids is that an effect known as edge weakness can be avoided. When using electrolytes for the electroless deposition of metal layers which comprise heavy metal ions as stabilizers at high convection of the electrolyte a decreased deposition of metal at the edges of the substrate occurs. This is deemed to be related to an increased assembly of the heavy metal ions used as stabilizers in these areas. This effect deteriorates the outline accuracy of the plating. Surprisingly, by the use of β-amino acids as stabilizers in electroless plating methods this edge weakening effect can be avoided which significantly increases the overall outline accuracy of the plating especially when plating large substrates.

In particular, β-amino acids having a $pK_a$-value within a range of 4 to 8, preferably within a range of 5 to 7 seems to be suitable in this respect. In particular, 3-amino propionic acid (β-alanin), 3-aminobutyric acid, 3-amino-4-methyl valeric acid and 2-aminoethane-sulfonic acid (Taurin) are usable.

The β-amino acid can be comprised in the inventive electrolyte within a range of 1 mg/l to 2 g/l, preferably 100 mg/l to 1 g/l, and even more preferred 200 mg/l to 400 mg/l.

As reducing agent in the inventive electrolyte a reducing agent of the group consisting of sodium hypophosphite, formaldehyde, dimethylaminoborane, aminoborane, or other organic boranes can be comprised.

As a metal ion source in the inventive electrolyte, advantageously a metal compound of the group consisting metal chloride, metal sulfate, metal acetate, metal nitrate, metal propionate, metal formiate, metal oxalate, metal citrate, and metal ascorbinate can be used, i.e., the source of cations of the metal to be deposited may comprise the counter anion of any of such salts. Here, especially, the metal compounds having volatile ions, like for example metal acetate, metal nitrate, metal propionate, and metal formiate are preferred since the volatile character of the anion those anions leak out from the electrolyte in gaseous form which enables to reduce the amount of anions in the electrolyte. This enables to extend the lifetime of the electrolyte significantly, which under normal conditions is only limited. For example, by the use of volatile anions also at a metal turnover rate of 22 metal layers having internal compressive stress can be deposited.

As a complexing agent the inventive electrolyte comprises a compound of the group consisting of 2-hydroxy propionic acid, propanedioic acid (malonic acid), EDTA, and amino acetic acid.

Preferably, the inventive electrolyte comprises an accelerator, which may preferably comprise a compound of the group consisting of saccharin, hydantoin, rhodanine, or carbamide and its derivates.

As metal to be deposited the inventive electrolyte may comprise a metal of the group consisting of nickel, copper, cobalt, boron and gold. By an appropriate choice of the metal to be deposited also alloys like for example nickel/cobalt-alloys, nickel/phosphor-alloys, cobalt/phosphor-alloys, boron/phosphorus-alloys or the like can be deposited. Also, the deposition of nickel/PTFE-layers or boron carbide/graphite-layers from dispersion bathes is possible by the inventive electrolyte.

The inventive electrolyte can have a pH-value within a range of pH 3 and pH 12, preferably within pH 3,9 and pH 6.

The temperature at which the electrolyte is used for deposition may vary between room temperature and 100° C.

The inventive electrolyte as well as the inventive method for the electroless deposition of metal layers on substrates are explained in terms of examples in the following, while the electrolyte as well as the method cannot be restricted to these embodiments only.

In preferred embodiments, the formulation of the invention contains a carboxyl component other than the carboxyl moiety of the β-amino acid. For example, the formulation may separately contain a monocarboxylic, dicarboxylic, or tricarboxylic organic acid. This component can comprise an aryl carboxylic acid, an aliphatic carboxylic acid, or a heterocyclic carboxylic acid. Among the suitable aliphatic carboxylic acids are fatty acids, α-hydroxycarboxylic acids, including α-hydroxy dicarboxylic acids particularly $C_1$ to $C_4$, α,β-unsaturated carboxylic acids, particularly $C_1$ to $C_4$ and especially acrylic.

Most preferably, the formulation of the invention comprises an organic stabilizer for electroless plating processes comprising an organic molecule which is the condensation product (adduct) of at least one β-amino acid and at least one carboxyl component which may be introduced into the aqueous medium as, e.g., the free carboxylic acid or a salt thereof.

The condensation product of the β-amino acid (e.g. β-alanine) and a carboxylic functional group as derived for the carboxylic acid or its salt, is a β-amide. The condensation product is present in a monomeric, oligomeric and/or polymeric form, i.e., as the N-terminal amide of a β-amino acid monomer, dimer, trimer, oligopeptide and polypeptide.

Amorphous metals (metallic glasses/glassy metals) are metallic materials having a disordered atomic-scale structure. Amorphous metals are non-crystalline and have an improved resistance to corrosion and wear, because of the absence of grain boundaries, and they are of a single class of metal.

An electrolytic bath, with a single class of metal, containing the stabilizer of the present invention leads to deposited metal layers, having properties like an amorphous metal. These properties are, for example, that these layers have no edge weakness effect; they are very passive; have a good resistance against corrosion; wear-resistance; and good compressive stress properties.

Further benefits of the stabilizer according to the present invention are, that it is metal free; provides a deposit having significantly better corrosion resistance including excellent resistance vs. nitric acid; is environmental friendly (non-toxic additive); has a higher phosphorus concentration at given pH level; and lower plating temperatures can be used to achieve the same plating speed and phosphorus content.

Preferably, the β-amino acid is a compound of the group consisting of 3-amino propionic acid (β-alanine), 3-aminobutyric acid, 3-amino-4-methyl valeric acid and 2-aminoethanesulfonic acid (taurine).

While amino acids, for example β-alanine, work effectively as a stabilizer, they may not act directly as stabilizer when initially added to the solution, or not be as effective as desired for this purpose. An improvement of stability can be achieved after a certain time. However when β-alanine is pre-mixed with lactic acid (or glycine, malic acid) it works immediately as stabilizer. It has been discovered that the carboxylic acid reacts with the β-alanine to form an amide structure. This structure element acts as a more effective stabilizer.

In preferred embodiments of the present invention, the carboxylic acid is a compound of the group consisting of acrylic acids, aromatic carboxylic acids, fatty acids, aliphatic carboxylic acids, keto acids, dicarboxylic acids, tricarboxylic acids, straight chain carboxylic acids, heterocyclic carboxylic acids, saturated carboxylic acids, unsaturated carboxylic acids, and α-hydroxy acids. It is also possible to use other organic compounds having a carboxylic functional group. In particular, the salts of carboxylic acids (carboxylate anion—$RCO_2^-$) can be used.

Another object of the present invention is a formulation (electrolyte) for the electroless deposition of a metal layer on a substrate, comprising a metal ion source for the metal to be deposited, a reducing agent, a complexing agent, an accelerator, and a stabilizer, wherein the stabilizer is an β-amino acid, and wherein the electrolyte comprises at least one additional carboxylic acid and/or at least one salt of an carboxylic acid.

In contrast to known electrolyte solutions the electrolyte of the present invention is self stabilising. Therefore it is not necessary to use various stabilizers and/or great quantities of stabilizers. It is an advantage of the present invention that it is almost not possible to overdose the stabilizer, when using the electrolyte according to the present invention.

The inventive formulation (electrolyte) comprising at least one additional carboxylic acid and/or at least one salt of a carboxylic acid shows various advantages. For example a metal layer deposited using the electrolyte according to the present invention exhibits an improved corrosion resistance. Hitherto, in the state of the art acidic acid salt spray [AASS] tests by 25 μm for about 150 hours are known. Using the electrolyte according to the present invention metal layers can be deposited on a surface of a substance that resist for more than 1000 hours in a acidic acid salt spray [AASS] test.

An edge weakness effect could not be observed, if the electrolyte comprises at least one carboxylic acid and/or at least one salt of a carboxylic acid.

It has been found that β-amino acids are capable to replace heavy metal stabilizers, cyanides, selenium compounds as well as sulfur compounds comprising sulfur in an oxidation state between −2 and +5 in electrolytes for the electroless deposition of metal layers, totally.

It has further found out that the use of β-amino acids, for example in a range of <0.5 g/L, in connection with a carboxylic acid leads to β-amides. These compounds could be present in a polymeric form or oligomeric form, as well as in a mixture thereof. A bath containing the inventive electrolyte is very stable, and generates metal layers with improved properties.

As reducing agent, the inventive electrolyte preferably contains, a reducing agent of the group consisting of sodium hypophosphite, formaldehyde, dimethylaminoborane, aminoborane, or other organic boranes can be comprised.

The reducing agent is consumed during the reduction. Hence it is necessary to refill the consumed reducing agent. Using the electrolyte according to the present invention it is possible to reduce the loss of reduction agent by half. Therefore it is possible to use about 15% less reducing agent, such as sodium hypophosphite.

Preferred the electrolyte comprises sodium hypophosphite with a concentration of 10 to 25 g/L, and even more preferably with a concentration of 12 to 18 g/L.

As a metal ion source in the inventive electrolyte that comprises a carboxyl component and/or an amide of a β-amino acid, the same metal compounds can advantageously be used as described above, i.e., a metal compound of the group consisting metal chloride, metal sulfate, metal acetate, metal nitrate, metal propionate, metal formiate, metal oxalate, metal citrate, and metal ascorbinate can be used. Here, especially, the metal compounds having volatile ions, like for example metal acetate, metal nitrate, metal propionate, and metal formiate are preferred since the volatile character of the anion those anions leak out from the electrolyte in gaseous form which enables to reduce the amount of anions in the electrolyte. This enables to extend the lifetime of the electrolyte significantly, which under normal conditions is only limited. For example, by the use of volatile anions also at a metal turnover rate of 22=i.e. 110 G Ni/L metal Layers having internal compressive stress can be deposited.

In the electroless plating formulations that contain a carboxyl component and/or an amide of a β-amino acid, the peferred $pK_a$ value of the amino acid, the selection of amino acid, the total equivalent concentration of β-amino acid, the pH of the electrolyte (formulation), the temperature at which the electrolyte is used for deposition, the nature and selection of the complexing agent, the nature and selection of the accelerator, and other features of the formulation and its use in electroless plating are as described hereinabove.

In a preferred embodiment of the invention the electrolyte according to the present invention comprises:
  13.03 g/L nickel sulfate;
  1.925 mg/L potassium iodite;
  17.27 g/L lactic acid;
  5.94 g/L malic acid;
  40.2 g/L sodium hypophosphite;
  9.81 g/L sodium hydroxide;
  0.35 g/L β-alanine
wherein the pH is in a range of pH 4 to pH 7.

Furthermore the object of the present invention is solved by a method for the electroless deposition of a metal layer on a substrate from an electrolyte according to the present invention, wherein sodium hypophosphite is used as a reducing agent.

Preferably, a sodium hypophosphite reducing agent is present in a concentration of 5 to 100 g/L, and even more preferably at a concentration of 20 to 60 g/L, is used as reducing agent.

Another object of the present invention is a metal layer on a surface of a substrate deposed by a method according to the present invention, wherein the phosphorous content of the metal layer is 2-6%, 6-10% or >10.5%. The amount of phosphorous has a considerable effect on the properties of the metal layer. A high phosphorous content of the metal layer leads to improved properties, for example improved corrosion resistance and a lower phosphorous content for example improved hardness of the metal layer.

A further property of a metal layer according to the present invention is that it is very passive.

A further advantage of the metal layers according to the present invention is the good residual compressive stress.

A further object of the present invention is the use of a stabilizer according to the present invention and/or the method according to the present invention for the electroless deposition of a metal layer on a substrate surface.

The inventive electrolyte as well as the inventive method, for the electroless deposition of metal layers on substrates is explained in terms of an example in the following, while the electrolyte as well as the method cannot be restricted to these embodiments only.

The stabilizer according to the present invention is especially suitable for the deposition of nickel layers. Especially in electroless nickel plating process this high performance stabilizer shows various advantages. No metal stabilizer is needed, the amide stabilized bath shows better corrosion resistance and can be adapted to, so called hybrid systems containing nickel sulfate and/or nickel acetate.

No metals were added to the stabilizer, but it is possible that the stabilizer contains traces of cobalt.

The stabilizer works in the pH range from pH 2 to pH 12.

Using the stabilizer according to the present invention, it is possible to yield metal layers having various phosphorus content: low phosphorus, 3-5% (crystalline); middle phosphorus, 5-7 (9) % (partially crystalline); high phosphorus, >10% (amorphous).

Further in accordance with the invention, it has been discovered that a β-amino acid is effective as a stabilizer at relative concentrations in the plating bath that are substantially lower than the concentrations of stabilizer typically used in the prior art. This avoids "overdosing" of stabilizer which may unduly limit the reactivity of the cation and compromise the productivity of a process in which the electrolyte formulation of the invention is used for electroless plating. However, it has also been found that there is little or no adverse effect of a "overdosing," i.e., using a higher than necessary stabilizer concentration, where the stabilizer comprises a substantial concentration of a carboxyl component, and especially where the β-amino acid has been substantially converted to an amide of a carboxyl component of the bath.

It has been found that β-amino acids are effective against wild depositions where the ratio of the total equivalent β-amino acid concentration to the molar concentration of the reducing agent is as low as about 0.002 equivalents per mole reducing agent. Generally preferred ranges for the ratio of total equivalent β-amino acid concentration to reducing agent are between about 0.002 and about 0.10 or between about 0.02 and about 0.10, more preferably between about 0.003 and about 0.08 or between about 0.03 and about 0.08 equivalents/mole. In order to assure against "overdosing," it is particularly preferred that the ratio of total equivalent β-amino acid concentration to reducing agent concentration is no greater than about 0.07, e.g., between about 0.002 and about 0.07, more preferably not greater than about 0.05, e.g., between about 0.003 and about 0.05, still more preferably not greater than about 0.03 equivalents/mole.

However, where the β-amino acid is tied up in the form of an amide, higher total concentrations of equivalent β-amino acid can be tolerated, e.g., in the range between about 0.002 and about 0.2 total equivalent β-amino acid per mole reducing agent. Within this range, a total equivalent β-amino acid to reducing agent ratio of not greater than 0.15 equivalents/mole, not greater than 0.10 equivalents per mole, not greater than 0.07 equivalents/mole, not greater than 0.05 equivalents/mole, or not greater than about 0.03 equivalents per mole, remains preferred, with a minimum concentration ratio of preferably at least about 0.003 equivalents per mole.

In order to assure a relatively high conversion of β-amino acid, β-amino acid oligomer, β-amino acid polymer and/or salts of the monomer, oligomer or polymer to the corresponding amide, the ratio of total equivalent β-amino acid content to total equivalent carboxyl component is preferably relatively low, i.e., there is a substantial excess of the carboxyl component, which comprises a carboxylic acid, carboxylate anions, a mixture of carboxylic acids and carboxylic anions, as well as amides and esters resulting from condensation of carboxyl groups with amines or alcohols in the formulation. Since the β-amino acid itself is a carboxyl component, the relationship between β-amino acid residues and carboxyl residues is usefully expressed as the ratio of total equivalent β-amino acid concentration to the difference between the total equivalent carboxyl component concentration and the total equivalent β-amino acid concentration. The difference which constitutes the denominator of this relationship is sometimes referred to herein as the "carboxyl differential."

It will be understood that the term "total equivalent β-amino acid concentration" refers to the total concentration of β-amino acid residues in the formulation, whether in the form of the amino acid, amino acid salt, amide formed by reaction of the β-amino acid with a carboxyl moiety, salts of such amides, oligomers, salts of oligomers, polymers, salts of polymers, N-terminal amides of oligomers or polymers, etc. Similarly, the term "total equivalent carboxyl concentration" refers to the total concentration of carboxyl residues in the formulation whether present as the carboxylic acid, carboxylic acid salt, amide, salt of amide, oligomer amides, polymer amides, or oligomer or polymer amide salts. The "carboxyl component" is the combination of all these various sources, or potential sources, of carboxyl moieties.

The preferred ratio of total equivalent β-amino acid to the carboxyl differential is governed by the equilibrium constant for the amide formation reaction, a parameter which in turn may depend on the pH and other parameters of the formulation. Generally, the ratio of the total equivalent β-amino acid concentration to the carboxyl differential is in the range between about 0.001 and about 0.5. Within that range, the ratio is preferably not greater than about 0.4, more preferably not greater than about 0.3, still more preferably not greater than about 0.2 or 0.10. In order to both drive the conversion of β-amino acid to the corresponding acid and avoid overdosing if the conversion is less than complete, it is particularly preferred that the ratio of the total equivalent β-amino acid concentration to the carboxyl differential be not greater than about 0.07, 0.05 or 0.03, and especially desirable that it be maintained at a level not greater than about 0.028, more preferably not greater than about 0.025, most preferably not greater than about 0.020. Preferably, the ratio is at least about 0.002 or 0.003, e.g., from about 0.002 to about 0.10, or from about 0.003 to about 0.3.

In order to maintain a high amide content, it is preferred that the pH of the formulation (electrolyte) is between about 4 and about 6. Equilibrium conversion of carboxylic acid and amine to amide is generally favored in this pH range.

The relatively low equivalent β-amino acid concentration in the formulations of the invention may be further defined by reference to ratio of the total equivalent β-amino acid concentration to the sum of the concentrations of cations of the metal to be deposited from the electroless plating bath. It is generally preferred that this ratio fall between about 0.01 and about 0.2 equivalents per mole, or between about 0.02 and about 0.2 equivalents/mole. Within those ranges, the ratio of equivalent β-amino acid to sum of cation concentrations is preferably no greater than about 0.15, more preferably not greater than about 0.10 and most preferably not greater than about 0.08 equivalents/mole.

The invention encompasses all combinations of the above stated ratios of total equivalent β-amino acid to reducing agent, total equivalent β-amino acid to the equivalent carboxyl differential, and total equivalent β-amino acid to the sum of reducible metal cation concentrations, and particularly so in the preferred formulations that include an accelerator.

It is further generally preferred that the total equivalent concentration of β-amino acid in the plating bath is not greater than about 1.2 g/l., e.g., in the range of about 0.05 to about 1.2 g/l. Within that range, the total equivalent β-amino acid concentration is preferably not greater than about 0.5 g/l. In such formulations, the concentration of reducing agent is preferably between about 0.05 and about 1.25 moles/l., e.g., between about 5 and about 100 g/l Na hypophosphite. More preferably the reducing agent content is between about 0.20 and about 0.70 moles/l, e.g., between about 20 and about 60 g/l. Na hypophosphite.

Thus, as a further example, a preferred plating composition comprises between about 0.05 and about 0.2 moles/liter of the cation of a metal to be electrolessly deposited on a substrate, between about 0.05 and about 1.25 moles/liter of a reducing agent, between about 0.1 and about 2 moles/liter of a complexing agent, between about 0.002 and about 0.25 moles/liter of an accelerator, and between about 0.0005 and about 0.015 moles/liter total equivalent β-amino acid.

It is particularly preferred that the formulation of the invention include an α-hydroxy acid such as lactic acid. It has further been found advantageous to include the combination of an α-hydroxy monocarboxylic acid and an α-hydroxy dicarboxylic acid, for example, a combination of lactic acid and malic acid in the electrolyte formulations of the invention. Other common α-hydroxy monocarboxylic acids include glycolic, hydroxymethyl glycolic, hydroxybutanoic, hydroxypentanoic, glucuronic and gluconic acids. Other common α-hydroxy dicarboxylic acids include tartronic, tartaric, α-hydroxy gluteric and α-hydroxy adipic acids.

It has further been found that metal phosphor alloys of favorable corrosion resistance are deposited from formulations which contain only a single metal ion that is reducible from the plating solution by the reducing agent onto a surface in contact with the formulation under the conditions of electroless plating. Thus, in certain preferred embodiments of the invention, the formulation contains a material concentration of only a single such reducible cation.

The invention is further directed to a novel and advantageous process for the preparation of an electroless plating formulation. In accordance with the process, a β-amino acid is first contacted with a substantial excess of carboxylic acid or a salt thereof in an aqueous medium for condensation of the carboxyl group with the amine group of the amino acid to form the corresponding amide. The preferred ratios of equivalent β-amino acid to carboxyl component in the aqueous reaction medium are essentially the same as stated above for the preferred ratio of total equivalent β-amino acid concentration to the carboxyl differential in the plating formulations of the invention as described hereinabove. Preferably, one or more carboxylic acids are charged to the aqueous medium in a proportion between about 3.5 and about 10 equivalents carboxyl/l. followed by a β-amino acid in a proportion between about 0.01 and about 0.1 moles/l. A condensation reaction proceeds between the amine group of the β-amino acid and the carboxyl moiety of the carboxylic acid, thereby producing the corresponding amide.

The premixture may also contain other components of the electroless plating solution, including, e.g., the reducing agent, accelerator and a complexing agent. After the premixture has been prepared and the β-amino acid and carboxyl group reacted to form the amide, the electroless plating formulation is prepared by combining the premixture with a metal salt solution containing a cation of the metal to be deposited. Once the plating solution has been prepared in this manner, it can be used directly in an electroless plating operation.

In certain preferred embodiments of the invention, the metal ion is introduced into the plating solution by Donnan dialysis. Donnan dialysis is particularly suitable for the two step process in which a premixture is prepared by mixing the β-amino acid with a carboxylic acid or other carboxyl source in an aqueous medium that may also contain a reducing agent, a complexing agent, and an accelerator. In this operation, a first solution containing a cation of the metal to be deposited is passed tangentially along one side of dialysis membrane comprising a cation exchange resin, e.g., a resin bearing sulfonic acid groups to which the cation is attracted. A second solution containing another cation, e.g., a solution of NaOH, is passed tangentially along an opposite face of the membrane in a direction parallel to the membrane that is preferably countercurrent to the direction of flow of the solution containing the metal to be plated. Advantageously, the second solution contains components of the plating bath other than cations of the metal to be plated. Preferably, the second solution contains the reducing agent, the complexing agent, an accelerator, and the stabilizer. In a particularly advantageous embodiment, the second solution comprises a premixture containing an amide that has been prepared by contacting the β-amino acid with a carboxylic acid or carboxylic acid derivative.

The dialysis may conveniently be conducted under ambient conditions of temperature and pressure. Flow velocity of the solutions across the membrane is typically between about 0.25 and about 4 l/m²-min.

Ion exchange via the membrane proceeds in the dialysis unit with a cation of the second solution, e.g., an alkali metal ion such as Na$^+$being transferred to the first solution and the metal to be deposited in a subsequent electroless plating operation, e.g., Ni$^{+2}$ or Cu$^{+2}$, being transferred to the second solution. Transfer of the metal to be plated from the first solution to the second results in transforming the second solution to a formulation directly useful for electroless plating. As it exits the dialysis unit on the side of the membrane opposite from the side over which the first solution is passed, the second solution acquires a composition that is directly useful for electroless plating, subject as necessary to concentration, dilution or introduction of additional additives.

The first solution exits the dialysis unit as a relatively dilute caustic solution, e.g., 10 wt. % NaOH. The Donnan dialysis may be conducted according to the process more particularly described in US published application 2005/0194256 which is expressly incorporated herein by reference.

Donnan dialysis allows the formulation of the invention to be prepared from salts of the metal to be deposited that are highly soluble in an aqueous medium, without necessarily incorporating the counteranion of such salt, which may in some instances not be desired. In the Donnan dialysis only the cation is transferred through the membrane, and the solution to which it is transferred may predominantly contain a counteranion that is more acceptable in the plating formulation than the counteranion of soluble salt of the metal to be deposited, e.g., the soluble salt delivered to one side of the cation exchange membrane might be a sulfate whereas the counteranion on the side to which the cation is transferred may preferably be a hydroxide. In some cases the compound comprising an ion pair of the metal to be deposited and the acceptable anion may be of limited solubility in an aqueous medium. But where the cation is transferred by dialysis to a receiving solution that contains the desired cation, the presence of a complexing agent in the receiving solution prevents undesired precipitation of the ion pair, e.g., as a metal hydroxide.

EXAMPLE 1

At a temperature between 80° C. and 94° C. a substrate (steel sheet) was brought into contact with an electrolyte comprising:
12.5 g/l to 25,5 g/l nickel acetate-4-hydrate
30 g/l to 50 g/l sodium hypophosphite
32 g/l to 55 g/l lactic acid
0.5 g/l to 10 g/l malonic acid
2.5 g/l to 22 g/l sodium saccharin
0.1 g/l to 2 g/l potassium iodide and
200 mg/l to 400 mg/l β-alanin At a pH within a range of pH 4 to pH 5 from this electrolyte a semi glossy nickel layer was deposited on the substrate surface at a plating rate of 8 μm/h to 12 μm/h.

EXAMPLE 2

At a temperature between 80° C. and 94° C. a steel sheet is brought into contact with an electrolyte comprising:
12.5 g/l to 25.5 g/l nickel acetate-4-hydrate
30 g/l to 70 g/l sodium hypophosphite
10 g/l to 30 g/l glycine
10 g/l to 40 g/l of an 25% by weight aqueous ammonia solution
0.2 to 0.8 g/l potassium iodide and
200 mg/l to 400 mg/l β-alanin At a pH within a range of pH 5 to pH 7 from this electrolyte a semi glossy nickel layer was deposited on the substrate surface at a plating rate of 15 μm/h to 40 μm/h, depending on the temperature of the electrolyte.

EXAMPLE 3

Plastic samples made from ABS etched with chromosulfuric acid and activated with a Pd-activator system were brought into contact with an electrolyte comprising:
10 g/l copper sulfate
8 g/l sodium hydroxide
10 g/l formaldehyde (as 37% by weight solution in $H_2O$)
26 g/l quadrol (commercially available from BASF AG)
2.5 g/l sodium iodide
200 mg/l β-alanin From the above mentioned electrolyte, a copper layer with a thickness of about 0.4 to 0.6 μm was plated on the substrate within 20 min at a temperature of 40° C. The plating result was fully comparable to the plating result achieved when depositing a copper layer under equal conditions on an ABS plastic substrate from an electrolyte commercially available as Enthone Enplate CU872, wherein Enthone Enplate CU872 comprises heavy metal ions.

Additionally, in the above mentioned example, copper sulfate can be replaced by copper chloride in an equal molar amount. The resulting electrolyte is not only free of sulfur compounds having an oxidation state between −2 and +5, but entirely free of sulfur.

EXAMPLE 4

Brass samples were degreased in an alkaline degreasing solution and activated in 10% sulfuric acid, rinsed and brought into contact with an electrolyte comprising:
5 g/l copper sulfate
4 g/l sodium hydroxide
10 g/l formaldehyde (as 37% by weight solution in $H_2O$)
400 mg/l β-alanin
11 g/l quadrol At a temperature of 80° C. from this electrolyte within 20 min a copper layer having a thickness of about 0.5 μm was deposited on the brass surface.

In an alternative example the quadrol [a N, N, N, N-Tetrakis(2-hydroxypropyl)ethylene diamine] comprised in the electrolyte was exchanged by 15-20 g/l of tetra sodium ethylene diamine tetra acetic acid ($Na_4EDTA$). The plating result was almost the same as by the use of quadrol.

EXAMPLE 5

At a temperature of about 85° C. and a pH in the range between pH 4-5 a steel sheet was brought into contact with an electrolyte comprising:
- 10 g/l to 28 g/l nickel sulfate-6-hydrate
- 30 g/l to 50 g/l sodium hypophosphite
- 32 g/l to 55 g/l lactic acid
- 0.5 g/l to 10 g/l malonic acid
- 2.5 g/l to 22 g/l sodium saccharin
- 0.1 g/l to 2 g/l potassium iodide and
- 200 mg/l to 400 mg/l β-alanin At a plating rate of about 9 μm/h a semi glossy nickel layer was deposited on the steel surface.

EXAMPLE 6

At a temperature of 40° C., a copper substrate is brought into contact with an electrolyte having a pH-value of about 10 which comprises:
- 25 g/l nickelacetate-4-hydrate
- 30 g/l citric acid
- 30 g/l sodiumhypophosphite
- 1 g/l dimethylaminoborane
- 7 g/l glycine
- 200 mg/l (β-alanine.

From this electrolyte a satin nickel layer was spontaneously deposited at a plating rate of about 2.5 μm/h. No skip-plating has occurred. The electrolyte has shown a high stability over a long term.

The same electrolyte was used to deposit a nickel layer on a brass substrate with the same results achieved when plating copper substrates.

EXAMPLE 7

- 6,7 g/l copper(II)chloride dihydrate
- 23 g/l quadrol
- 8.9 g/l formaldehyde (as 37% by weight solution in $H_2O$)
- 8.2 g/l sodiumhydroxide
- 200 mg/l (β-alanine From the above mentioned electrolyte, a copper layer with a thickness of about 0.4 to 0.6 μm was plated on the substrate within 20 min at a temperature of 40° C. The plating result was fully comparable to the plating result achieved when depositing a copper layer under equal conditions on an ABS plastic substrate from an electrolyte commercially available as Enthone Enplate CU872, wherein Enthone Enplate CU872 comprises heavy metal ions.

EXAMPLE 8

Plastic samples made from ABS etched with chromosulfuric acid and activated with a Pd-activator system were brought into contact with an electrolyte comprising:
- 10 g/l sodiumhydroxide
- 10 ml/l formaldehyde (as 37% by weight solution in $H_2O$
- 23 g/l quadrol (N, N, N', N'-Tetrakis(2-hydroxypropyl) ethylenediamine)
- 200-400 mg/l β-alanine Addition of Copper:

The copper was added to this electrolyte prior to contacting the ABS samples via Donnan dialysis via alkaline stable cation selective ion exchange membrane to the electrolyte. As copper source a coppersulfate solution is used. The plating solution and coppersulfate solution counterflowed through the dialysis membrane system. Sodium ions in the plating solution were replaced by copper ions from copper sulfate solution without dragging in/out the counter (hydroxide & sulfate) ions. The flow velocity was 1 l/m²-min. tangentially across the ion exchange membrane surface until the copper concentration in the bath reaches 2.5 g/l. After then the dialysis was only switched on if the copper concentration was lower than 2.3 g/l.

Maintaining of the electroless copper electrolyte -replenishment of parts of hydroxide. In order to stop the increase of salt freight during plating an additional Donnan dialysis was performed. This dialysis system used for this additional dialysis consisted of an alkaline stable anion exchange membranes. Formiate and $CO_3^{2-}$-Ions (unwanted by-products) were replaced selectively by hydroxide which is used for the electroless copper deposit reaction.

The plating solution and sodiumhydroxide solution (20 g/l) were counterflowed. The flow velocity was 1-2 $l/(m^2*h)$ for the plating solution and 0.5-1 $l/(m^2*h)$ for the NaOH solution. The exchange rate was 7-15 g(NaOH)/($h*m^2$) (related to the concentration of formiate and carbonate in the bath.

By help of the dialysis the drift to a higher salt freight was stopped.

As plating result a copper layer having a thickness of 0.4 μm was deposited within 25 min at a temperature of 40° C. on the plastic substrates.

EXAMPLE 9

1. Pre-mixture of complexing agents, hypophosphite and/ or accelerator including stabilizer formation (part B):
   - 200-400 g/L sodium hypophosphite;
   - 100-500 g/L NaOH;
   - 200-500 g/L lactic acid;
   - 100-200 g/L malic acid; and
   - 2-5 g/L β-alanine.
2. Pre-mixture of reduction agent component and stabilizer (part C):
   - 500-800 g/L sodium hypophosphite;
   - 25-250 g/L sodium hydroxide;
   - 25-100 g/L lactic acid;
   - 10-80 g/L malic acid; and
   - 5-15 g/L β-alanine.
3. Pre-mixture of nickel salts (part A):
   - 300-550 g/L $NiSO_4*6\,H_2O$; and
   - 50-445 g/L Ni $(OOCCH_3)_2*4\,H_2O$ Pre-mixture 1 and 2 are prepared and mixed for at least 15 min in order to achieve a full reaction of the acids with the β-alanine in order to form the amide. Then 100-150 g/L of part B, and 30-100 ml/L of part A are mixed and heated to 70-95° C.

Part C and part A are used for replenishment. Normally in the ration 1:1.

Permissible variations in proportions and alternatives in elements of the Invention: Plating electrolyte composition: 3-6 g/L $Ni^{2+}$; 25-40 g/L sodium hypophosphite; pH 4 to pH 9; 400-1200 mg/L stabilizer.

EXAMPLE 10

Electrolyte composition for the electroless deposition of a nickel layer on a substrate, containing:
- 13.03 g/L nickel sulfate;
- 1.925 mg/L potassium iodide;
- 17.27 g/L lactic acid;
- 5.94 g/L malic acid;
- 40.2 g/L sodium hypophosphite;
- 9.81 g/L sodium hydroxide;
- 0.35 g/L β-alanine;

wherein the pH is in a range of pH 4 to pH 7.

Use of the electrolyte according to the present invention leads to metal layers having a phosphorus content of >10.5%.

What is claimed is:

1. A method for the electroless deposition of a metal layer on a substrate comprising contacting the substrate to be plated with a plating formulation comprising a metal ion source for the metal to be deposited, a reducing agent, a complexing agent, an accelerator, and a β-amino acid and/or β-amino acid derivative as stabilizer, wherein the β-amino acid is present within a range of 1 mg/L to 2 g/L and wherein the metal to be deposited comprises nickel, copper, cobalt, boron, or gold, or an alloy of nickel, copper, cobalt, boron, or gold.

2. The method of claim 1 wherein the β-amino acid and/or derivative has a pKa value within a range of 4 to 8.

3. The method of claim 1 wherein the β-amino acid is an acid of the group consisting of 3-aminopropionic acid, 3-aminobutyric acid, 3-amino-4-methylvaleric acid, and 2-aminoethanesulfonic acid.

4. The method of claim 1 wherein the reducing agent is a compound of the group consisting of sodium hypophosphite, formaldehyde, dimethyl aminoborane, amino borane, and other organic boranes.

5. The method of claim 1 wherein the plating formulation comprises as a complexing agent a compound of the group consisting of 2-hydroxy propionic acid, propanedioic acid (malonic acid), EDTA and amino acetic acid.

6. The method of claim 1 wherein the plating formulation as an accelerator comprises a compound of the group consisting of saccharine, hydantoin, rhodanine, carbamide and carbamide derivates.

7. The method of claim 1 wherein the plating formulation is free of inorganic stabilizers, specifically free of lead, bismuth, antimony, zinc and/or tin.

8. The method of claim 1 wherein the metal to be deposited is a metal of the group consisting of nickel, copper, cobalt, boron, gold or an alloy comprising at least one of these metals.

9. The method of claim 1 wherein the plating formulation is free of cyanides, selenium compounds and sulfur compounds comprising sulfur in an oxidation state between −2 and +5.

10. The method of claim 1 wherein the plating formulation further comprises at least one additional carboxylic acid and/or at least one salt of a carboxylic acid.

11. The method of claim 10 wherein the carboxylic acid is a compound of the group consisting of acrylic acids, aromatic carboxylic acids, fatty acids, aliphatic carboxylic acids, keto acids, dicarboxylic acids, tricarboxylic acids, straight chained carboxylic acids, heterocyclic carboxylic acids, saturated carboxylic acids, unsaturated carboxylic acids, and α-hydroxy acids.

12. The method of claim 1 wherein the β-amino acid is a compound of the group consisting of 3-amino propionic acid, 3-aminobutyric acid, 3-amino-4-methyl valeric acid and 2-aminoethane-sulfonic acid.

13. The method of claim 1 wherein the plating formulation comprises <0.5 g/L β-amino acid.

14. The method of claim 1 wherein the plating formulation comprises:
- 13.03 g/L nickel sulfate;
- 1.925 mg/L potassium iodite;
- 17.27 g/L lactic acid;
- 5.94 g/L malic acid;
- 40.2 g/L sodium hypophosphite;
- 9.81 g/L sodium hydroxide;
- 0.35 g/L β-alanine;

wherein the pH is in a range of pH 4 to pH 7.

15. The method of claim 1 wherein the ratio of the total equivalent (β-amino acid concentration to the molar concentration of said reducing agent being no greater than about 0.07 equivalents/mole.

16. The method of claim 1 wherein the stabilizer comprises a (β-amino acid derivative selected from the group consisting of (β-amino acid salts, (β-amino acid amides, salts of (β-amino acid amides, oligomers of said acids and salts, polymers of said acids and salts, and combinations thereof.

17. The method of claim 1 wherein said stabilizer comprises a β-amino acid selected from the group consisting of 3-aminopropionic acid, 3-aminobutyric acid, 3-amino-4-methylvaleric acid, and 2-aminoethanesulfonic acid, a derivative of 3-aminopropionic acid, 3-aminobutyric acid, 3-amino-4-methylvaleric acid, or 2-aminoethanesulfonic acid, or combinations thereof.

18. The method of claim 1 wherein the plating formulation further comprises at least one additional carboxyl compound selected from the group consisting of carboxylic acids and salts thereof, the ratio of the total equivalent β-amino acid concentration to the difference between the total equivalent carboxyl concentration of the formulation and said total equivalent β-amino acid concentration being not greater than about 0.028.

19. The method of claim 1 wherein the plating formulation comprises:
- the metal ion source for the metal to be deposited;
- the reducing agent, wherein the reducing agent is a compound of the group consisting of sodium hypophosphite, formaldehyde, dimethyl aminoborane, amino borane, and other organic boranes
- the complexing agent, wherein the complexing agent comprises a compound of the group consisting of 2-hydroxy propionic acid, propanedioic acid (malonic acid), EDTA and amino acetic acid;
- the accelerator, wherein the accelerator comprises a compound of the group consisting of saccharine, hydantoin, rhodanine, carbamide and carbamide derivates;
- the β-amino acid and/or β-amino acid derivative as stabilizer, wherein the β-amino acid and/or β-amino acid derivative has a pKa value within the range of 4 to 8;
- wherein the electrolyte is free of inorganic stabilizers of lead, bismuth, antimony, zinc and/or tin.

20. The method of claim 19 wherein the plating formulation comprises:
- the metal ion source for the metal to be deposited;
- the reducing agent, wherein the reducing agent is sodium hypophosphite in a concentration between 5 and 100 g/L;
- the complexing agent, wherein the complexing agent comprises a compound of the group consisting of 2-hydroxy propionic acid, propanedioic acid (malonic acid), EDTA and amino acetic acid;

the accelerator, wherein the accelerator comprises a compound of the group consisting of saccharine, hydantoin, rhodanine, carbamide and carbamide derivates;

the β-amino acid and/or β-amino acid derivative as stabilizer, wherein the β-amino acid and/or β-amino acid derivative has a pKa value within the range of 4 to 8;

wherein the electrolyte is free of cyanides, selenium compounds and sulfur compounds comprising sulfur in an oxidation state between −2 and +5;

wherein the ratio of the total equivalent β-amino acid concentration to the molar concentration of said reducing agent is no greater than about 0.07 equivalents/mole; and the ratio of the total equivalent β-amino acid concentration to the difference between the total equivalent carboxyl concentration of the formulation and said total equivalent β-amino acid concentration being not greater than about 0.028.

21. The method of claim 1 wherein the plating formulation comprises β-amino acid within a range of 100 mg/L to 1 g/L.

22. The method of claim 1 wherein the β-amino acid is an acid of the group consisting of 3-aminopropionic acid, 3-aminobutyric acid, and 3-amino-4-methylvaleric acid.

23. The method of claim 1 wherein the metal to be deposited is nickel or an alloy thereof.

24. The method of claim 1 wherein the metal to be deposited is copper or an alloy thereof.

* * * * *